Jan. 30, 1968 F. W. ANDERSON Plant Pat. 2,793
NECTARINE TREE
Filed Nov. 16, 1966
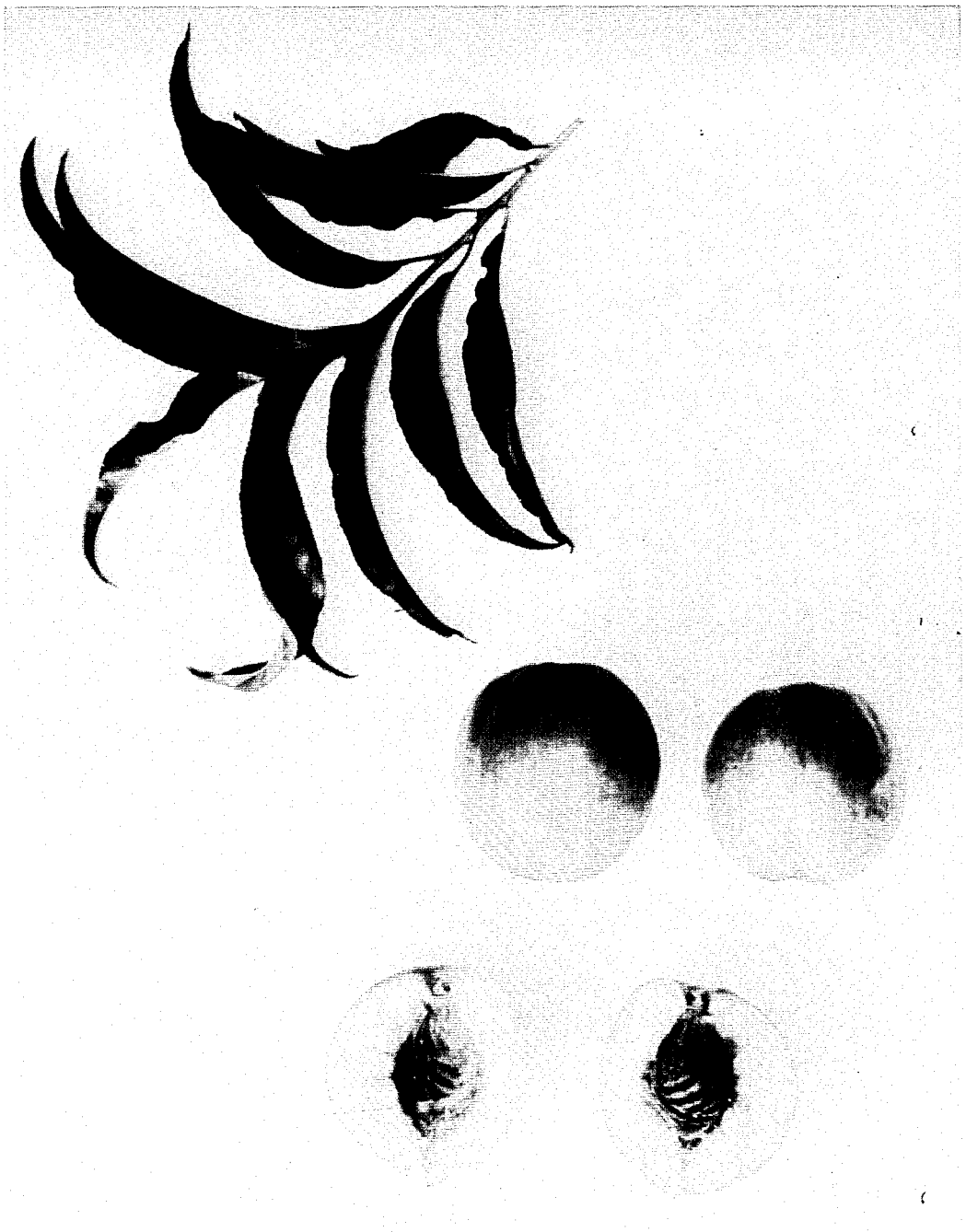
INVENTOR
Frederic W. Anderson
BY
Webster & Webster
ATTORNEYS United States Patent Office Plant Pat. 2,793
Patented Jan. 30, 1968

2,793
NECTARINE TREE

Frederic W. Anderson, Merced, Calif., assignor to Stark Bros Nurseries and Orchards Co., Louisiana, Mo., a corporation of Missouri Filed Nov. 16, 1966, Ser. No. 594,949
1 Claim. (Cl. Pit.—41)

This invention relates to a new and distinct variety of nectarine tree which is large, vigorous, and a regular bearer of large, globose, freestone fruit having yellow flesh and yellow skin substantially overspread with red at maturity. The variety is embraced by group 111 (with a bitter kernel) in the classification established by Caillavet and Souty in their Monographie des Principales Variétés de Pêchers, 1950 edition.

The present variety of nectarine trees is essentially characterized, as to novelty, by the fact of its large, globose, freestone fruit having a ripening period approximately with the Late Le Grand (United States Plant Patent No. 1,035) clingstone nectarine, and slightly later than the Elberta (unpatented) freestone peach.

The herein claimed variety of nectarine tree was originated by me in my experimental orchard located near Le Grand, Merced County, Calif., as a cross between the Late Le Grand nectarine and the Early Sun Grand (United States Plant Patent No. 1,420) nectarine; such cross having been accomplished under conditions of accurate and effective control.

Under continuing and close observation, the variety was recognized by me as having substantial potential for commercial growing, and I, therefore, undertook asexual reproduction of the variety; this having been accomplished by top-working on a mature orchard tree in my experimental orchard located as aforesaid. Such asexual reproduction established the continuity of and ran true to the original tree in all respects.

The drawing is an illustration, by photographic reproduction in color, of a twig with leaves, two whole fruits, and another fruit cut in half to show the flesh and with the stone remaining in one half.

Referring now more specifically to the pomological details of this new and distinct variety of nectarine tree, the following is an outline description thereof; all major color plate identifications, by comparison with fresh specimens, being by reference to Maerz and Paul Dictionary of Color.

Tree:
- *Size.*—Large.
- *Vigor.*—Vigorous.
- *Growth.*—Spreading.
- *Density.*—Open.
- *Production.*—Very productive.
- *Bearing.*—Regular bearer.

Trunk: Size—medium.

Branches:
- *Size.*—Medium.
- *Lenticels.*—Number—medium.

Leaves:
- *Size.*—Medium to large. Average length—4½" to 5". Average width—1⅛" to 1¼".
- *Form.*—Lanceolate; acutely pointed.
- *Margin.*—Crenate.
- *Petiole.*—Medium length.
- *Glands.*—Average number and position—usually 2 on petiole and 1–3 on blade. Size—medium. Form—reniform.

- *Color.*—Top side—medium green (23–L–7). Under side—lighter green (22–L–5).

Flower buds: Size—medium.

Flowers:
- *Blooming period.*—Date of first bloom—Mar. 6, 1966. Date of full bloom—Mar. 15, 1966.
- *Size.*—Large.

Fruit:
- *Maturity when described.*—Hard ripe.
- *Date of first picking.*—July 29, 1966.
- *Date of last picking.*—Aug. 8, 1966.
- *Size.*—Uniform; large. Average diameter axially—2¾". Average transversely in suture plane—2¾".
- *Form.*—Uniform; symmetrical; globose.
- *Suture.*—Distinct; shallow.
- *Ventral surface.*—Rounded slightly.
- *Cavity.*—Medium depth; medium breadth.
- *Apex.*—Short.

Skin:
- *Thickness.*—Medium to thick.
- *Texture.*—Medium to tough.
- *Tendency to crack.*—Slight.
- *Down.*—Wanting.
- *Color.*—Yellow (11–L–5), substantially overspread with red (5–L–5) shading somewhat darker in full maturity; the red being partially streaked and mottled.

Flesh:
- *Amygdalin.*—Wanting.
- *Texture.*—Medium to firm; meaty.
- *Fibers.*—Few.
- *Ripens.*—Evenly.
- *Flavor.*—Subacid.
- *Aroma.*—Distinct to wanting.
- *Eating quality.*—Good to best.
- *Color.*—Yellow (11–L–4) slightly streaked with red (5–K–6) adjacent pit cavity. Color of pit cavity, red (5–K–6).

Stone:
- *Type.*—Free.
- *Size.*—Medium to large. Average length—1¼". Average breadth—1". Average thickness—¾".
- *Form.*—Oblong to oval.
- *Sides.*—Equal.
- *Ridges.*—Rounded.
- *Tendency to split.*—Slight.
- *Kernel.*—Bitter.
- *Color.*—Brown (8–L–7).

Use: Market; dessert.
Keeping quality: Good.
Shipping quality: Good.

The tree and its fruit herein described may vary in slight detail due to climatic and soil conditions under which the variety may be grown; the present description being of the variety as grown in the Central Valley of California.

The following is claimed:

A new and distinct variety of nectarine tree, substantially as illustrated and described, which is large, vigorous, and a regular and very productive bearer of large, globose, freestone fruit having yellow flesh and yellow skin substantially overspread with red in maturity; the ripening period of the fruit being approximately with the Late Le Grand clingstone nectarine and slightly later than the Elberta freestone peach.

No references cited.

ROBERT E. BAGWILL, *Primary Examiner.*